United States Patent [19]
Katahara et al.

[11] Patent Number: 5,670,878
[45] Date of Patent: Sep. 23, 1997

[54] INSPECTING A CONDUCTIVE OBJECT WITH A STEADY STATE MAGNETIC FIELD AND INDUCED EDDY CURRENT

[75] Inventors: Keith W. Katahara, Allen; Pedro F. Lara, Dallas; Kenneth R. Riggs, Richardson, all of Tex.

[73] Assignee: Atlantic Richfield Company, Los Angeles, Calif.

[21] Appl. No.: 80,295

[22] Filed: Jun. 21, 1993

[51] Int. Cl.$^6$ .......................... G01N 27/72; G01N 27/82; G01R 33/12
[52] U.S. Cl. .......................... 324/221; 324/232; 324/240
[58] Field of Search .......................... 324/346, 219, 324/220, 221, 232, 240, 241, 242, 243

[56] References Cited

U.S. PATENT DOCUMENTS

| | | | |
|---|---|---|---|
| 2,346,830 | 4/1944 | De Lanty | 324/232 |
| 4,188,577 | 2/1980 | Mhatre et al. | 324/232 |
| 4,990,851 | 2/1991 | Spies | 324/242 |
| 5,038,107 | 8/1991 | Gianzero et al. | 324/346 |

FOREIGN PATENT DOCUMENTS

| 1043481 | 9/1983 | U.S.S.R. | 324/239 |
|---|---|---|---|

*Primary Examiner*—Walter E. Snow
*Attorney, Agent, or Firm*—Wofford, Fails, Zobal & Mantooth

[57] ABSTRACT

There is provided a transient electromagnetic method and apparatus for inspecting objects. The apparatus includes a sensing portion, which has a transmitting antenna and at least one receiving antenna thereon. The sensing portion is located adjacent to the object which is to be inspected such that the antennas are adjacent to the object. There is also a magnet located adjacent to the sensing portion. The magnet has poles located adjacent to the object, so as to provide a steady-state magnetic field to the object. By applying a steady-state magnetic field to the object during inspection, increased inspection speeds and improved spatial resolutions can be achieved. In addition, casing can be inspected from inside of tubing.

10 Claims, 3 Drawing Sheets

INSPECTING A CONDUCTIVE OBJECT WITH A STEADY STATE MAGNETIC FIELD AND INDUCED EDDY CURRENT

SPECIFICATION

1. Field of the Invention

The present invention relates to electromagnetic diffusion methods and apparatuses for non-destructively inspecting objects, such as pipelines, tubing, storage tanks, etc., for corrosion and other flaws.

2. Background of the Invention

The use of transient electromagnetic or electromagnetic diffusion techniques to inspect containers such as pipelines is disclosed in Lara U.S. Pat. No. 4,843,319 and in Spies U.S. Pat. No. 4,843,320, which patents are owned by the assignee of the present invention. The '319 and '320 patents are directed to a transient electromagnetic method for detecting corrosion on conductive objects such as pipelines. Often, such objects are wrapped in insulation to either prevent undue heat loss or to protect personnel from hazards. The transient electromagnetic method can penetrate the insulation to probe the conductive wall underneath. This layer of insulation may vary in thickness from one location to another along the container wall. The '319 patent further provides a method for compensating for variations in the thickness of insulation.

The transient electromagnetic method of the '319 and '320 patents requires placing a transmitting antenna and a receiving antenna in proximity to the object to be inspected. The transmitting antenna then induces a current, which current diffuses into the object wall and decays rapidly. The decay of the induced current is detected by the receiving antenna. By analyzing the induced current decay, a measurement of the wall thickness of the object under test can be obtained. Corrosion acts to reduce wall thickness, thus any reduction in wall thickness can be determined from the transient electromagnetic measurement.

The transient electromagnetic inspection method of the '319 and '320 patents is unconcerned with the speed of data acquisition. However, there exist many situations where speed of the inspection process is of primary concern. This is particularly true in downhole tubing, heat exchanger tubing and buried fluid transmission pipelines where, because of the situs of the tubing or pipeline, the antennas must be located interiorly of the tubing or pipeline. As a result of using interiorly located antennas, downtime is incurred. Lengthy downtimes produced by the use of stationary antennas are costly and are therefore avoided in practice.

Prior art technologies other than transient electromagnetic methods are not very satisfactory for inspecting downhole tubing and the like. Ultrasonic methods have narrow resolutions that add to inspection time. Also, the ultrasonic transducers are affected by fluid coupling from the fluid inside of the tubing or pipeline. Flux leakage methods have no such coupling problem, but there is a problem with interpreting the data. The signals are strongly affected by sharp edges, which make interpretation difficult.

Transient electromagnetic methods do not suffer these disadvantages. Therefore, it is desirable to increase the speed of transient electromagnetic inspections of an object. With such an inspection system, larger areas could be inspected within shorter periods of time. Furthermore, with such an inspection system, the antennas could be placed inside of pipelines and not impede the flow of fluid. Thus, the pipelines undergoing inspection could remain in use.

In addition to inspection speed considerations, it is also desirable to inspect casing in production oil and gas wells. Such inspections must take place with the antenna sensors located inside of tubing, which tubing is located inside of the casing. Thus, the wall of the tubing is interposed between the casing wall, which is to be inspected, and the sensors. The tubing is typically made of carbon steel and serves to shield the sensors from electromagnetic signals outside of the tubing. In order to inspect the casing, the tubing must be pulled out of the well, a costly and time consuming procedure.

SUMMARY OF THE INVENTION

It is an object of the present invention to provide an electromagnetic diffusion method and apparatus for inspecting an object, wherein the speed of inspection is increased.

It is a further object of the present invention to provide an electromagnetic diffusion method and apparatus wherein sensors that are located inside of tubing can inspect a casing wall outside of and surrounding the tubing.

The method of the present invention inspects a conductive object by subjecting a portion of the object to a steady-state magnetic field, inducing an eddy current into the subjected object portion with an abruptly changing current and detecting the induced eddy current in the object portion.

In one aspect of the present invention, the method further includes the step of continuing to subject the object portion to the steady-state magnetic field during the step of detecting the induced current in the object portion. In still another aspect of the present invention, the magnetic field is provided by a magnet that is located in proximity to the object portion and a transmitting antenna and a receiving antenna are provided in proximity to the object portion. The transmitting antenna, the receiving antenna and the magnet are moved during the inspection process.

In another aspect of the present invention, the method inspects a conductive object through a conductive shield. A portion of the shield is subjected to a steady-state magnetic field. An eddy current is induced into a portion of the object that is adjacent to the subjected shield portion through the shield with an abruptly changing current. The induced eddy current is detected in the object portion through the shield.

The apparatus of the present invention includes a sensing portion that has a transmitting antenna and a receiving antenna, a transmitter that produces an abruptly changing current and that is connected to the transmitting antenna, a receiver that is connected to the receiving antenna and a steady-state magnet located adjacent to the transmitting antenna.

In one aspect of the apparatus, the magnet has two poles and the sensing portion is located between the poles.

BRIEF DESCRIPTION OF THE DRAWINGS

FIG. 3 is a front side view of a sensor head assembly.

FIG. 4 is a cross-sectional view of the transmitting and receiving coil arrangement.

FIG. 5 is a cross-sectional view of a receiving coil arrangement.

DESCRIPTION OF PREFERRED EMBODIMENTS

Generally speaking, to probe a conductive object such as a wall using transient electromagnetic techniques, an electromagnetic transmitting source and a receiving sensor are required. The transmitting and receiving elements are located adjacent to the wall and the transmitting source is provided with an abruptly changing current. The transmitting source induces a current into the wall, which induced current is detected by the receiving sensor. A received signal is produced by the receiving sensor that represents the induced current. This received signal is then analyzed to determine the thickness of the wall at the sensor location. By knowing the original thickness of the wall, a reduction in thickness can be discovered. If it is found that the wall thickness has been reduced, then the presence of corrosion or some other thickness reducing mechanism can be deduced.

Use of transient electromagnetic methods and apparatuses are shown and described in U.S. Pat. Nos. 4,843,319, 4,843,320 and 4,839,593, the disclosures of which are incorporated herein by reference.

Figure 1:
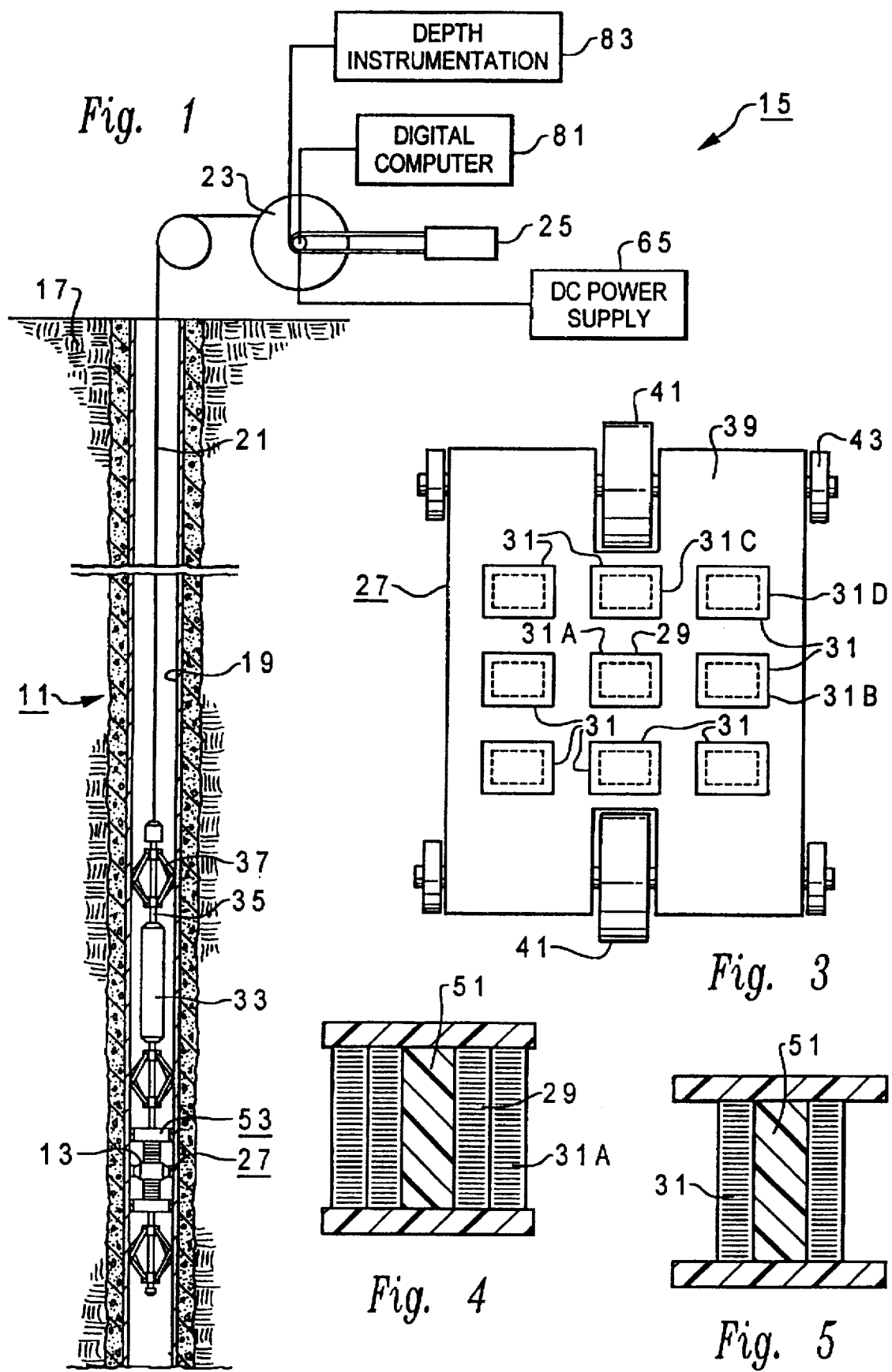
FIG. 1 is a cross-sectional side view of a borehole and surface equipment, showing the apparatus of the present invention, in accordance with a preferred embodiment.

In FIG. 1, there is shown a schematic longitudinal cross-sectional view of a cased well borehole 11, showing an electromagnetic logging apparatus 13 located therein, and supporting surface equipment 15, with which the method of the present invention, in accordance with a preferred embodiment, can be practiced.

The well borehole 11, which is drilled into the earth 17, is an oil or gas well. The well borehole 11 is lined with a length of casing 19 that is cemented in place in the borehole. The casing 19 is made of a conductive material such as steel.

The logging apparatus 13 is located within the casing 19 and moves up and down the borehole for logging operations. The logging apparatus 13 is suspended inside of the casing 19 by a logging cable 21, which provides electrical power and data communications channels from the surface equipment 15. On the surface, the logging cable is wound around a drum 23. A motor 25 rotates the drum to lower and raise the logging apparatus 13 inside of the borehole 11.

The logging apparatus 13 includes plural sensing heads 27, downhole electronics 33, and a body member 35. The sensing heads each contain transmitting and receiving antennas 29, 31. The body member 35 is cylindrical and elongated. Centralizers 37 are positioned along the body member 35 to maintain the logging apparatus in a centered position along the longitudinal axis of the casing 19.

Figure 2:
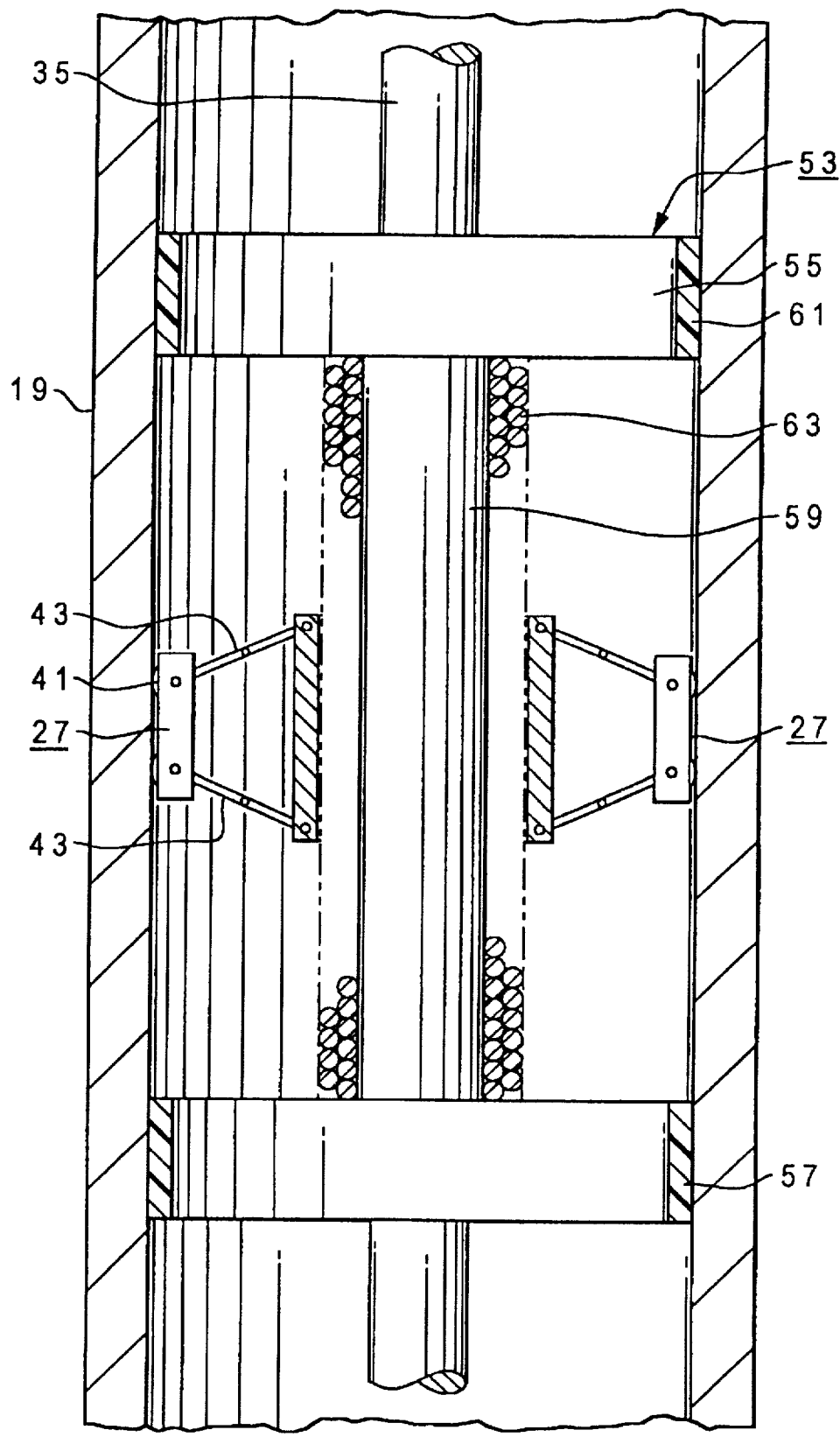
FIG. 2 is a close-up side view of the downhole apparatus.

Referring to FIGS. 2 and 3, there may be provided plural sensing heads 27, wherein the sensing heads 27 are disposed around the circumference of the logging apparatus 13 and are large enough to provide 360 degrees circumferential coverage of the casing. To prevent contact between adjacent sensing heads, the sensing heads 27 are longitudinally displaced from each other along the body member. Thus, there is an upper pair of sensing heads and a lower pair of sensing heads. Each pair has two diametrically opposed sensing heads. The lower pair is rotated 90 degrees from the upper pair to provide for complete circumferential coverage. Each sensing head has an arcuately shaped outer surface 39 that approximately corresponds to the curvature of the inside surface of the casing 19. Each sensing head 27 has a pair of rollers 41 thereon for contact with the casing 19 (see FIG. 3). The rollers 41 protect the antennas 29, 31 from abrasion with the casing wall 19. It is preferred to located the antennas as close as possible to the casing wall in order to increase resolution. As an alternative to the rollers, materials that perform well under abrasion are available. Each sensing head 27 is mounted onto the body member 35 by a pair of arms 43. The arms 43, which are spring loaded, force the sensing head into rolling contact with the inside surface of the casing.

Each sensing head 27 (see FIG. 3) has plural antennas located thereon so as to be adjacent to the casing wall. In the center of each sensing head 27 is a transmitting antenna 29 and a coincident receiving antenna 31A. Both transmitting and receiving antennas 29, 31A are wound onto the same core 51, as shown in FIG. 4. The core 51, which is in the shape of a spool, is made of a non-magnetic and non-conductive material such as plastic. The respective antennas are made up of respective coils of wire. There are also provided plural receiving antennas located around the central transmitting antenna 29. Each receiving antenna 31 is made up of a coil of wire wrapped onto a core 51 (see FIG. 5). The antennas are oriented in the sensing head 27 so that the longitudinal axes of the cores 51 are perpendicular to the adjacent portion of casing walls. In addition, receiving antennas having their longitudinal axes are oriented so as to be parallel to the adjacent wall are provided. Thus, at each receiving antenna location, there are two receiving antennas, with one being oriented perpendicular to the wall and the other being oriented parallel to the wall.

The receiving antennas 31 other than the coincident antenna 31A are placed in various spatial orientations with respect to the transmitting antenna 29. Thus, there are receiving antennas 31B that are located laterally or transversely from the transmitting antenna 29. The transverse antennas 31B are located along a first imaginary line extending between the respective transverse antenna and the transmitting antenna 29, which first imaginary line is perpendicular to the direction of motion of the transmitting antenna. There are also receiving antennas 31C that are located longitudinally from the transmitting antenna 29. The longitudinal antennas 31C are located along a second imaginary line extending between the respective longitudinal antenna and the transmitting antenna 29, which second imaginary line is parallel to the direction of motion of the transmitting antenna. And there are receiving antennas 31D that are located both transversely and longitudinally (diagonally) from the transmitting antenna 29.

Referring to FIG. 2, the sensing heads 27 are located between the poles of a magnet 53. In the preferred embodiment, the magnet is an electromagnet. The electromagnet 53 has an upper pole piece 55 and a lower pole piece 57. The pole pieces 55, 57, which are disc shaped, extend radially outward from the body member 35. A core sleeve 59 physically and magnetically couples the pole pieces together. The pole pieces and the core are made up of a material (such as iron) that is high in magnetic permeability so as to allow for a magnetic field. The pole pieces 55, 57 are sized so as to have a diameter that is slightly smaller than the inside diameter of the casing 19. Plastic end pieces 61 can be provided in the gap between the pole pieces and the casing so as to reduce wear caused by contact between the pole pieces and the casing. The magnetic permeability of the gap can be enhanced by mixing iron powder with the plastic to form the pieces 61. For example, the composition of the end pieces 61 could be 50% or more of iron powder. Alternatively, wire brushes could be used in the gap between the pole pieces and the casing.

A wire coil 63 is wrapped around the core 59. The coil 63 is connected to a dc power supply 65 (see FIG. 1), which provides a dc current through the coil. The power supply may be located on the surface or downhole. The sensing heads 27 are coupled to a collar 67 that is coupled to the magnet.

The magnet 53 need not be an electromagnet. It could be some other type of temporary magnet or it could be a permanent magnet. However, it is believed that stronger magnetic fields would be available with an electromagnet. Also, use of an electromagnet allows the magnetic field to be controlled on and off, so that the magnet can be more easily lowered downhole when the magnetic field is off. If need be, plural magnets could be used to obtain stronger magnetic fields.

In addition, plural magnets can be provided, with each magnet arranged in a unique orientation so as to provide steady-state magnetic fields in plural directional components. The use of magnetic fields in plural directions more fully saturates the object being inspected. It is preferable to provide steady-state magnetic fields in two orthogonal components. For example, the magnet 53 shown in FIG. 2 creates a magnetic field that is oriented longitudinally along the length of the casing 19. A second magnet could be provided so as to create a magnetic field that is oriented circumferentially around the casing 19. Such a magnet would have two poles positioned 180 degrees apart around the circumference of the logging apparatus 13. Thus, the poles would have a positioning arrangement similar to the two sensing heads 27 shown in FIG. 2.

Figure 6:
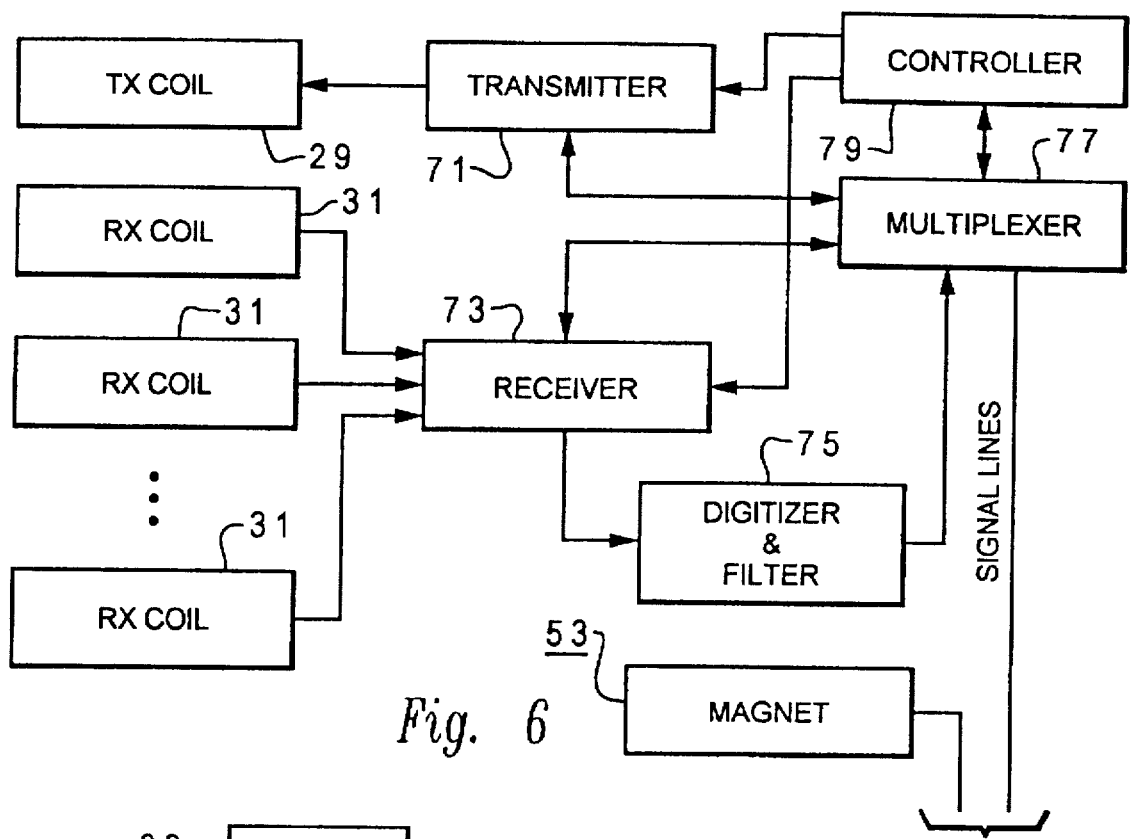
FIG. 6 is a block diagram of the downhole electronics.

In FIG. 6, there is shown the transmitting and receiving antennas, that are contained in a sensing head, as connected to the downhole electronics. The transmitting antenna 29 in each sensing head 27 is connected to a transmitter 71. The transmitter 71 generates a pulse having abrupt fall times on the order of 1–100 microseconds. Typically, the pulse has amplitudes of one to two amps. The pulses of the transmitter pulse train alternate polarity to eliminate dc bias in the instrumentation. Thus, the first pulse is positive, the second pulse is negative, the third pulse is positive, the fourth pulse is negative and so on. The duration of each pulse is sufficiently long to stabilize the pulse magnitude so that there are no currents induced into the casing wall before the occurrence of the abrupt fall time of the pulse.

The respective receiving antennas 31 of each sensing head 27 are connected to a receiver 73. The receiver 73 is a multi-channel instrument, having a channel for each receiving antenna. The receiver 73 is a broad band instrument with a wide (5 or 6 order of magnitude) dynamic range. An analog-to-digital converter 75 digitizes the data from each receiving antenna. The digitized data is filtered for 60 Hz noise rejection and sent to a multiplexer 77 for transmission up the logging cable 21.

The downhole electronics may contain as many transmitters and receivers as required. In the preferred embodiment, there are four transmitting antennas 29, one for each sensing head 27. One transmitter may energize all four transmitting antennas; either simultaneously or sequentially, or plural transmitters may be used. Likewise, plural receivers may be used, to provide an appropriate number of receiver channels. An appropriate number of digitizers is also provided. A controller 79 is connected to the transmitter 71 and the receiver 73. The controller 79 coordinates data acquisition by the sensing heads by controlling the transmitter 71 and the receiver 73.

The surface equipment includes the drum 23 and the motor 25 (which are described above), a digital computer 81 and depth instrumentation 83 (see FIG. 1). On the surface, the data is received from the logging cable by the computer. The computer 81 is a conventional portable computer with sufficient memory capacity to record the data. The computer stores the data from the receiving antennas and performs some processing of the data. The depth instrumentation 83 tracks the depth of the logging apparatus in the hole.

The method of inspecting the wall of the downhole casing will now be described, referring to FIGS. 1–6. The logging apparatus 13 is lowered down into the well 11 to the lowest point of inspection (see FIG. 1). Then, the magnet 53 is energized to produce a magnetic field. This is accomplished by providing dc current to the coil 63 from the power supply 65. The magnetic field is produced in the upper pole piece 55, across the gap between the upper pole piece and the casing wall, in the casing wall 19, across the gap between the lower pole piece, in the lower pole piece 57 and in the core 59.

Next, the logging apparatus 13 is raised toward the surface at a constant speed. This is accomplished with the motor 25 and drum 23. With the logging apparatus located inside of the well casing, the rollers 41 of the sensing heads 27 contact the inside surface of the casing wall 19 and the pole pieces 55, 57 of the magnet 53 are in close proximity to the casing wall. The sensing heads 27 are forced into rolling contact with the casing wall by the arms 43 such that there is a gap between the transmitting and receiving antennas and the casing wall. The transmitting and receiving antennas on the sensing head are maintained at a relatively constant distance from the casing wall 19.

As the logging apparatus 13 is raised uphole, the transmitting antenna 29 on each sensing head 27 is energized by the transmitter 71. Each transmitting antenna 29 is energized for a sufficient length of time to stabilize the current in the antenna, thereby insuring no currents are induced into the casing wall. Then, each transmitting antenna 29 is abruptly deenergized by the transmitter, so that the current in the transmitting antenna rapidly falls to zero magnitude. This abrupt deenergization of the transmitting antenna induces current into that portion of the casing wall 19 that is adjacent to the respective transmitting antenna.

As soon as the respective transmitting antenna is deenergized, the receiver 73 (FIG. 6) that is associated with the adjacent receiving antennas 31 is switched on. The respective receiving antennas 31 detect the presence of and the decay of the induced current in the casing wall and produce a respective received signal representing the induced current. The received signals are received by the receiver 73, where they are amplified and filtered, and then digitized by the digitizer 75. The received signals are then transmitted uphole over the logging cable by the multiplexer 77. At the surface (FIG. 1), the computer 81 stores the received signals. The computer 81 processes the received signals to obtain a measurement of wall thickness as described in U.S. Pat. Nos. 4,843,319, 4,843,320 and 4,839,593.

When the eddy currents are induced into the casing 19 by the transmitting antenna 29, the eddy currents are superimposed on a steady-state magnetic field which is produced in the casing by the magnet 53. It is believed that the magnetic field reduces the magnetic permeability or ferromagnetism of the casing wall by aligning the magnetic domains along the path of the magnetic field (which is vertical in FIG. 1). As the ferromagnetism of the casing wall decreases, the penetration and diffusion speeds of the eddy currents induced by the transmitting antenna increases. This is because the induced eddy currents do not interact with the magnetic domains of the casing wall. Faster penetration times allow faster inspection speeds. Thus, the logging apparatus 13 can be raised towards the surface at a faster speed when inspecting with the magnetic field. In addition, faster diffusion speeds increase the resolution of inspection by limiting the spatial diffusion of the induced eddy currents. Thus, the eddy currents are focused more into a narrow cone within the casing wall. When the magnetic field is strong, for example, greater than 20,000 gauss, the material in a casing wall has even been observed to act paramagnetically. Thus, the resolution of the tool is increased to the point wherein cracks can be detected in paramagnetic conductors.

The dc magnetic field is strong enough to saturate the wall. For example, for a casing wall, the dc magnetic field could be at least 1000 gauss.

The logging apparatus 13 is preferably moving along the casing wall during data acquisition in order to provide fast inspections. With the magnet arrangement shown in FIG. 2, the sensing heads are located between the poles of the magnet. This arrangement allows a steady-state magnetic field to be introduced into the casing wall before, during and after the eddy currents have been induced by the transmitting antenna 29 and their decay has been detected by the receiving antennas. For example, for a fixed point on the wall of the casing 19, the upper pole piece 55 passes the fixed point first, as the logging apparatus is raised to the surface. Thus, a steady-state magnetic field is provided at the fixed point in the casing. As the logging apparatus is raised further, a sensing head 27 passes the fixed point, wherein the transmitting antenna 29 induces eddy currents into the wall portion that includes the fixed point and that is subjected to the steady-state magnetic field. The receiving antennas 31 detect the decay of the induced currents while the wall portion is still subjected to the steady-state magnetic field. As the logging apparatus is raised even further, the lower pole piece 57 passes the fixed point in the casing, after which the steady-state magnetic field disappears from the fixed point.

Figure 7:
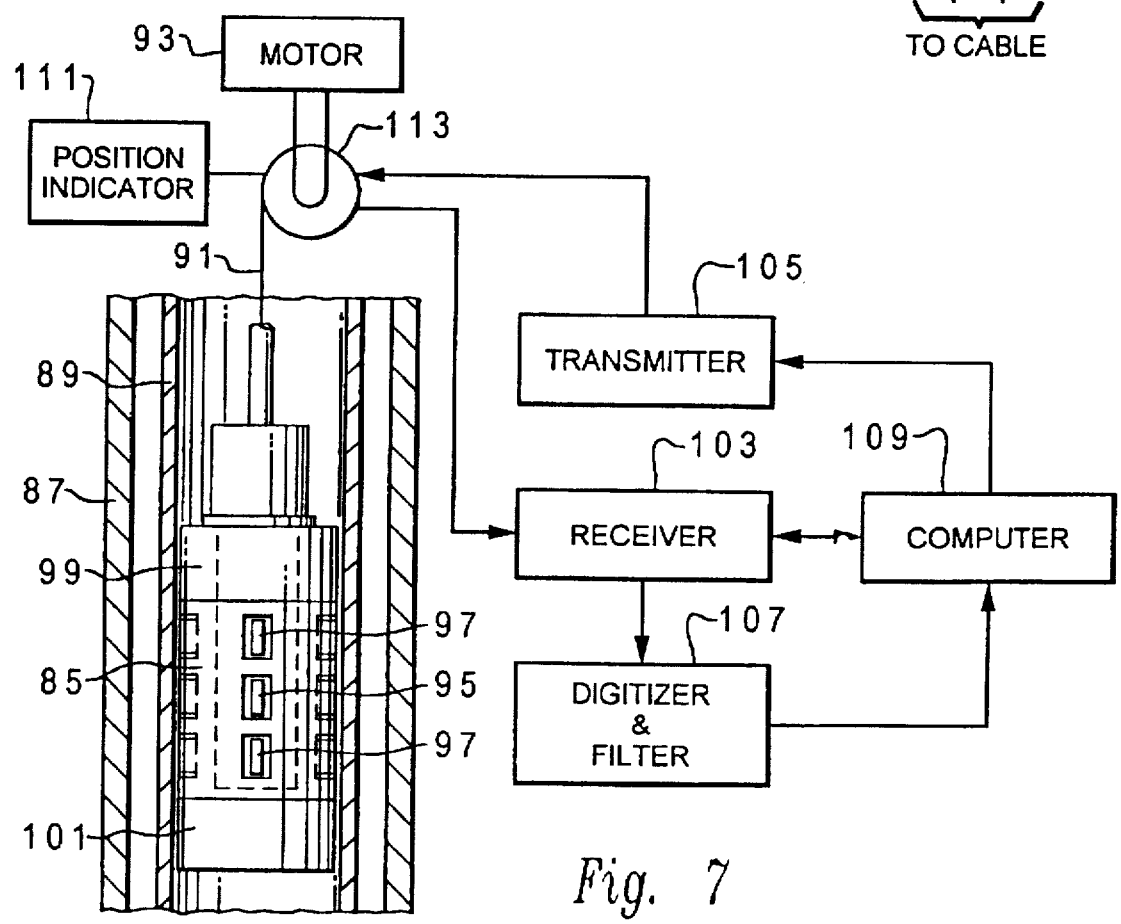
FIG. 7 is a schematic diagram showing the present invention in accordance with another embodiment.

In FIG. 7, there is shown the apparatus 85 of the present invention, as set up to inspect a segment of pipe 87. For longer lengths of pipe, the apparatus can be contained in a pig. The apparatus 85 is located within an inner pipe 89, so that the inner pipe is interposed between the pipe 87 which is to be inspected and the inspection apparatus 85. One example of this type of inspection arrangement occurs when inspecting the casing 87 in a production well. The logging apparatus 85 is located inside tubing 89. The apparatus 85 is moved through the piping 89 by a cable 91 and motor arrangement 93. The apparatus 85 has transmitting antennas 95 spaced 90 degrees apart around the outer circumference of the probe. Receiving antennas 97 are spaced longitudinally from each transmitting antenna. A magnet having an upper pole piece 99 and a lower pole piece 101 is provided, with the transmitting and receiving antennas located between the pole pieces. A receiver 103 and transmitter 105 are provided, as are a digitizer and filter 107 and a computer 109. A position indicator 111 is coupled to the drum 113 so as to allow a correlation between the data obtained and the position along the piping. As with the apparatus 13 of FIG. 1, plural magnets can be provided to provide steady-state magnetic fields in plural directional components.

The operation of the apparatus in FIG. 7 is the same as for the apparatus in FIG. 1.

With conventional inspection tools, the inner pipe 89 shields the outer pipe 87 from inspection. Thus, in order to inspect the outer pipe 87, the inner pipe 89 must be removed from the outer pipe 87. A similar shielding problem was discussed in U.S. Pat. No. 4,839,593, the disclosure of which has been incorporated herein by reference.

By providing a strong steady-state magnetic field to the inner pipe 89, the inner pipe is made paramagnetic relative to the outer pipe 87. Thus, the eddy currents induced into the inner pipe 89 by the transmitting antennas 95 will decay much faster than will the eddy currents into the outer pipe 87 by the transmitting antennas. At late times, the inner pipe 89 becomes effectively transparent, allowing the detection of the eddy currents in the outer pipe 87 by the receiving antennas 97. Thus, at late times, the decay of eddy currents in the outer pipe 87 are detected and processed. In addition, the inner pipe 89 does not shield the steady-state magnetic field from the outer pipe 87. Thus, the benefits of inspection with a steady-state magnetic field can be obtained in the outer pipe.

Although the receiving sensors have been described as antennas or coils, the receiving sensors could instead include magnetic flux sensors such as Hall effect devices.

Although the moving means for moving the transmitting antennas and the receiving antennas along the wall which is to be inspected has been described as a motor, drum and cable arrangement, other moving means may be used. Also, the transmitting and receiving antennas need not be located within a pipe or casing; they may be located on the exterior if circumstances permit such placement.

The foregoing disclosure and the showings made in the drawings are merely illustrative of the principles of this invention and are not to be interpreted in a limiting sense.

We claim:

1. A method of inspecting a conductive object, comprising the steps of:
    a) energizing a first coil with electrical current so as to subject a portion of said object to a steady-state magnetic field, wherein the inspection can be conducted faster;
    b) providing an abruptly changing current to a second coil so as to induce an eddy current into said subjected object portion;
    c) allowing said induced eddy current to decay while continuing to subject the portion of said object to said steady-state magnetic field;
    d) detecting said decay of said induced eddy current in said object portion.

2. The method of claim 1 further comprising the step of continuing to subject said object portion to said steady-state magnetic field during the step of detecting said induced current in said object portion.

3. The method of claim 1 wherein said step of subjecting a portion of said object to a steady-state magnetic field further comprises the step of locating a magnet in proximity to said object portion, said magnet providing a continuous steady-state magnetic field.

4. The method of claim 3 further comprising the step of locating a transmitting antenna and a receiving antenna in proximity to said object portion so as to induce an eddy current and detect said induced eddy current.

5. The method of claim 4 further comprising the step of moving said transmitting antenna, said receiving antenna and said magnet during said steps of subjecting a portion of said object to a steady-state magnetic field, inducing an eddy current into said subjected object portion and detecting said inducted eddy current.

6. A method of inspecting a conductive object through a conductive shield, comprising the steps of:
    a) energizing a first coil with electrical current so as to subject a portion of said shield to a steady-state magnetic field, wherein the inspection can be conducted faster;
    b) providing an abruptly changing current to a second coil so as to induce an eddy current into a portion of said object that is adjacent to said subjected shield portion through said shield;

c) allowing said induced eddy current to decay;

d) detecting said decay of said induced eddy current in said object portion through said shield.

7. The method of claim 6 wherein said step of subjecting a portion of said shield to a steady-state magnetic field further comprises the step of subjecting said object portion to said steady-state magnetic field.

8. The method of claim 6 further comprising the steps of:

a) locating a magnet in proximity to said shield so as to provide said magnetic field;

b) locating a transmitting antenna and a receiving antenna in proximity to said shield so as to induce an eddy current and detect said induced eddy current;

c) moving said transmitting antenna, said receiving antenna and said magnet during said steps of subjecting a portion of said shield to a steady-state magnetic field, inducing an eddy current and detecting said induced current.

9. An apparatus for inspecting a conductive object, comprising:

a) a sensing portion having a transmitting antenna and a receiving antenna;

b) a transmitter that produces an abruptly changing current, said abruptly changing current having a decay, said transmitter being connected to said transmitting antenna;

c) a receiver connected to said receiving antenna;

d) a controller for operating said receiver during the decay of said abruptly changing current;

e) a steady-state electromagnet located adjacent to said transmitting antenna, said electromagnet having a coil that is electrically separate from said transmitting antenna, said electromagnet allowing the inspection to be conducted faster.

10. The apparatus of claim 9 wherein said magnet has two poles and said sensing portion is located between said poles.

* * * * *